(12) United States Patent
McConnell et al.

(10) Patent No.: US 8,302,844 B2
(45) Date of Patent: Nov. 6, 2012

(54) WRAPPER HAVING A PREDETERMINED LINE OF WEAKNESS

(75) Inventors: Kimberly Nichole McConnell, Morrow, OH (US); Letha Margie Hines, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1009 days.

(21) Appl. No.: 11/602,112

(22) Filed: Nov. 20, 2006

(65) Prior Publication Data
US 2008/0118679 A1    May 22, 2008

(51) Int. Cl.
*B65D 65/28* (2006.01)
*A61F 13/20* (2006.01)
*B29D 22/00* (2006.01)

(52) U.S. Cl. ............... 229/87.05; 604/385.02; 428/35.7

(58) Field of Classification Search ............. 604/385.02; 206/210; 428/43–46, 34.1–36.92, 102–104, 428/188
See application file for complete search history.

(56) References Cited

U.S. PATENT DOCUMENTS

| | | | | |
|---|---|---|---|---|
| 3,973,567 A | * | 8/1976 | Srinivasan et al. | 604/385.05 |
| 4,170,305 A | | 10/1979 | Hull, Jr. et al. | |
| 4,648,513 A | | 3/1987 | Newman | |
| 4,726,805 A | * | 2/1988 | Sanders, III | 604/15 |
| 4,881,644 A | | 11/1989 | Norquest et al. | |
| 4,966,286 A | * | 10/1990 | Muckenfuhs | 206/494 |
| 5,133,457 A | | 7/1992 | Kadel | |
| 5,442,897 A | | 8/1995 | Hinzmann et al. | |
| 5,934,809 A | * | 8/1999 | Marbler | 383/208 |
| 6,293,932 B1 | | 9/2001 | Balzar et al. | |
| 6,478,763 B1 | | 11/2002 | Simonsen et al. | |
| 6,955,665 B2 | | 10/2005 | Domeier et al. | |
| 7,073,666 B2 | | 7/2006 | Arndt | |
| 7,101,358 B2 | | 9/2006 | Domeier et al. | |
| 2003/0065300 A1 | | 4/2003 | Suga | |
| 2003/0220624 A1 | | 11/2003 | Domeier et al. | |
| 2003/0220625 A1 | * | 11/2003 | Domeier et al. | 604/385.12 |
| 2003/0233813 A1 | | 12/2003 | Leslie et al. | |
| 2004/0133142 A1 | | 7/2004 | Lochte et al. | |
| 2006/0212015 A1 | | 9/2006 | Peele | |
| 2007/0156109 A1 | | 7/2007 | Loyd et al. | |

FOREIGN PATENT DOCUMENTS

| | | |
|---|---|---|
| EP | 0 213 241 A1 | 3/1987 |
| EP | 0 597 446 B1 | 4/1998 |
| EP | 0 807 075 B1 | 8/1999 |
| WO | WO 03/082174 A1 | 10/2003 |

OTHER PUBLICATIONS

PCT International Search Report dated Apr. 16, 2008.

* cited by examiner

*Primary Examiner* — Maria Veronica Ewald
*Assistant Examiner* — Prashant J Khatri
(74) *Attorney, Agent, or Firm* — Andrew J. Hagerty; Amanda T. Barry

(57) ABSTRACT

A package having a wrapper having a length, a top, a bottom, an outer surface having a periphery, a longitudinal axis, and one or more predetermined lines of weakness. The one or more predetermined lines of weakness can be disposed at an angle with respect to the longitudinal axis. The wrapper can enclose an article for feminine hygiene.

21 Claims, 4 Drawing Sheets

WRAPPER HAVING A PREDETERMINED LINE OF WEAKNESS

FIELD OF THE INVENTION

This invention relates to wrappers for articles for feminine hygiene, and more particularly, to wrappers having one or more predetermined lines of weakness.

BACKGROUND OF THE INVENTION

Articles for feminine hygiene, such as sanitary napkins, liners, tampons, interlabial pads, incontinence articles, and pessaries, are generally used by women for feminine needs, such as, e.g., to absorb menstrual or other body exudates, for pelvic support, and/or for other feminine needs. Such items are typically individually packaged to facilitate hygiene, ease of use, and ease of carrying. Tampons, for example, can be individually packaged into wrappers that fully enclose the tampon. The wrappers can be made of any suitable material, such as, for example, plastic film, such as film made of polyethylene, polypropylene or cellophane. The usual way of opening such wrappers is to separate or tear the wrapper to create an opening in the wrapper through which the tampon can be accessed.

Currently available wrappers can have one or more drawbacks. First, many wrappers separate into more than one piece of material upon opening. This type of wrapper generates several pieces of waste originating from the wrapper that have to be handled during use of the tampon, and then must be collected and disposed of. Second, wrappers can unpredictably tear in a manner that prevents reliable and consistent opening. Third, wrappers can undesirably open during transport and prior to use, such as, e.g., in a user's purse or pocket, which can result in a loss of hygiene and waste of the article. Fourth, many wrappers are not designed to facilitate use of the wrapper for discreet disposal of a portion of the article, such as a tampon applicator, after use. Fifth, many wrappers can be cumbersome to open and/or may not have intuitive opening means that are easy for a user to understand. Further, currently available wrappers typically expose a large portion of the article and/or the entire article when the wrapper is fully opened. This can result in a decreased hygienic environment during use of the article and/or after use of the article if the wrapper is configured to accept a portion of the article for disposal after use.

As such, it would be desirable to provide a wrapper for an article for feminine hygiene, such as, e.g., a tampon, that can provide increased hygiene, predictable and easy opening, discrete disposal, and that can remain in one piece after opening. It would also be desirable to provide a wrapper for an article for feminine hygiene that can provide reduced exposure of the article upon opening the wrapper.

SUMMARY OF THE INVENTION

A package having a wrapper having a length, a top, a bottom, an outer surface having a periphery, a longitudinal axis, and one or more predetermined lines of weakness disposed at an angle with respect to the longitudinal axis is provided. The one or more predetermined lines of weakness can extend around less than about 95% of the periphery of the outer surface of the wrapper and can be located more than about 5 mm from the top of the wrapper. The wrapper can enclose an article for feminine hygiene and the article can be released by breaking the one or more lines of weakness to form an opening. In certain embodiments, the wrapper can remain in one piece after the one or more lines of weakness are broken.

A package comprising a wrapper having a length, a top, a bottom, an outer surface having a periphery, and one or more predetermined lines of weakness, an upper third including the top, a middle third, and a bottom third including the bottom is further provided. The one or more predetermined lines of weakness can be disposed in the upper third of the wrapper and can extend around less than about 95% of the periphery. The wrapper can enclose an article configured for insertion into the vagina of a woman and the article can have an insertion end and a second end opposite the insertion end. At least a portion of the second end of the article can be disposed in the upper third of the wrapper. The article can be released by breaking the one or more lines of weakness to form an opening, and less than about 50% of the article can be located above the opening when the article is disposed in the wrapper at a position most proximal to the bottom of the wrapper. The wrapper can remain in one piece after the one or more lines of weakness are broken.

Also provided is a method of removing an article from a wrapper.

DETAILED DESCRIPTION OF THE INVENTION

Figure 1:
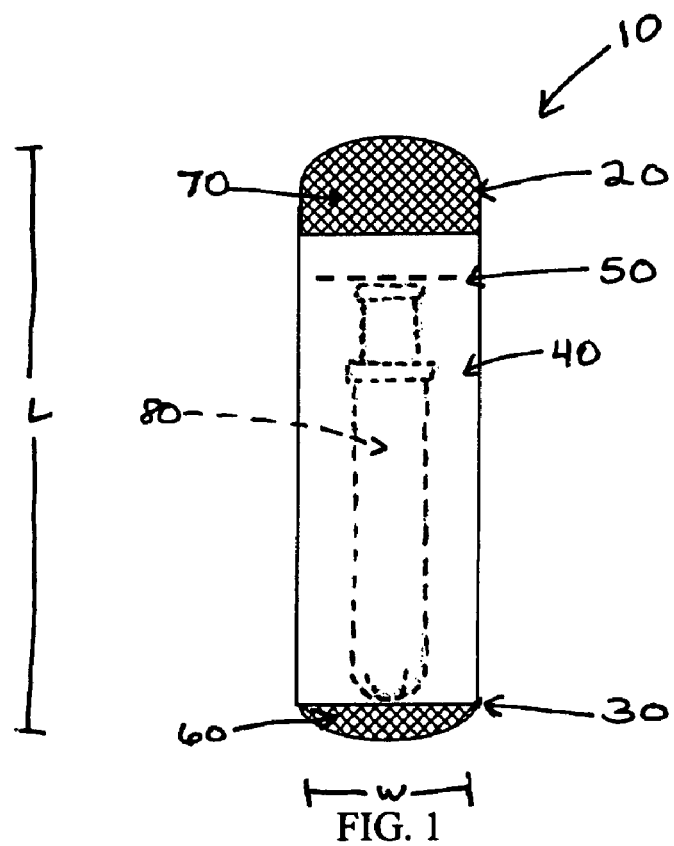
FIG. 1 is a plan view of one embodiment of the present invention.

The present invention relates to packages for articles, such as, e.g., articles for feminine hygiene, such as, e.g., tampons. The wrapper can include one or more predetermined lines of weakness. In certain embodiments, the one or more predetermined lines of weakness can be disposed at an angle with respect to a longitudinal axis of the wrapper. In addition, or alternatively, the one or more predetermined lines of weakness can be disposed substantially transverse with respect to the length of the wrapper. The wrapper can be configured to substantially enclose an article for feminine hygiene, such as, e.g., a tampon. In certain embodiments, the wrapper can be configured to individually package one article or can be configured to package more than one article. Such wrappers can provide benefits to a user such as reduced exposure of the article prior to use, increased hygiene, predictable and easy opening, and/or discrete disposal. The wrappers also can remain in one piece after opening, reducing the pieces of waste and increasing convenience to the user.

As used herein, the term "article for feminine hygiene" refers to articles that typically can be intended for feminine use, such as, e.g., absorbent articles, such as, e.g., sanitary napkins, liners, tampons, interlabial articles, incontinence articles; and pessaries.

As used herein, the term "tampon" refers to any type of absorbent structure such as, e.g., an absorbent mass, that can be inserted into the vaginal canal or other body cavity for the purpose of, such as, e.g., absorbing fluid, aiding in wound healing, and/or for delivering materials, such as moisture or active materials such as medicaments. The term "tampon" can also include the combination of an absorbent structure with any type of applicator that can be associated with the absorbent structure to facilitate insertion of a tampon into the vaginal canal or other body cavity. A tampon can include any known tampon configuration such as, for example, digital tampons, tampons with traditional plunger type applicators, and/or tampons with compact applicators, such as, e.g., tampons described in U.S. Pat. Nos. 4,726,805; 4,846,802; 4,960,417; 5,087,239; 5,279,541; 6,258,075; 6,478,763; or any other known tampon.

As used herein, the term "line of weakness" refers to a plurality of weakness points arranged in a pattern. The pattern can be straight, bent, angled, curved, and/or can change direction. One or more of the individual weakness points can overlap to form the line of weakness. In addition, or alternatively, one or more of the individual weakness points can be spaced apart from one another to form the line of weakness.

As used herein, the term "weakness point" refers to a region in the wrapper material where the thickness of the wrapper material is substantially less than the thickness of the wrapper material surrounding the region. Weakness points can be formed in any suitable manner, such as, e.g., by depressions or perforations.

As used herein, the term "depression" refers to a weakness point having a thickness less than the thickness of the surrounding wrapper material but greater than zero. The depressions can extend into the wrapper material from the inner and/or from the outer surface of the wrapper material. In certain embodiments, individual depressions can overlap each other when forming a line of weakness, so that a substantially continuous line of weakness formed by depressions is generated, such as, e.g., a score line or groove.

As used herein, the term "perforation" refers to one or more weakness points, wherein at least a portion of the region of the wrapper material forming the weakness point can have a thickness of about zero.

FIG. 1 shows one embodiment of a wrapper 10. The wrapper 10 has a length L, a width W, a top 20, a bottom 30, and an outer surface 40 having a periphery. In this embodiment, the wrapper 10 has a line of weakness 50 located in the upper third of the wrapper 10, such as, e.g., in the upper fourth of the wrapper 10. The line of weakness 50 can extend around less than about 50% of the periphery of the wrapper 10. The wrapper 10 can have an end seal 60 located at the bottom 30 of the wrapper 10 and/or a top seal 70 that can function as an opening aid, such as, e.g., a tab, such as, e.g., a finger grip, located at the top 20 of the wrapper 10. An article for feminine hygiene 80, such as, e.g., a tampon, can be disposed within the wrapper 10.

Figure 2:
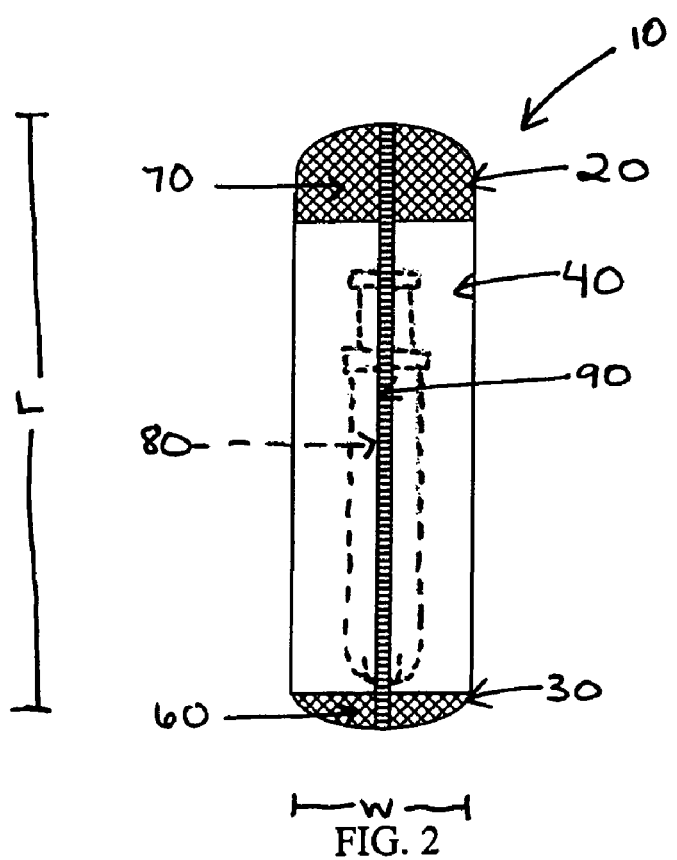
FIG. 2 is a plan view of one embodiment of the present invention.

FIG. 2 shows one embodiment of the back of the wrapper 10 of the present invention, such as, for example, the wrapper 10 shown in FIG. 1. The wrapper 10 has a length L, a width W, a top 20, a bottom 30, and an outer surface 40 having a periphery. In this embodiment, the wrapper 10 has a line of weakness 50 that can extend around less than about 50% of the periphery of the wrapper 10. The wrapper 10 can also have an end seal 60 located at the bottom 30 of the wrapper 10 and/or a top seal 70 that can function as an opening aid, such as, e.g., a tab, such as, e.g., a finger grip, located at the top 20 of the wrapper 10. In this embodiment, the wrapper 10 has a back seal 90 that extends down the length L of the wrapper 10. An article for feminine hygiene 80, such as, e.g., a tampon, can be disposed within the wrapper 10.

Figure 3:
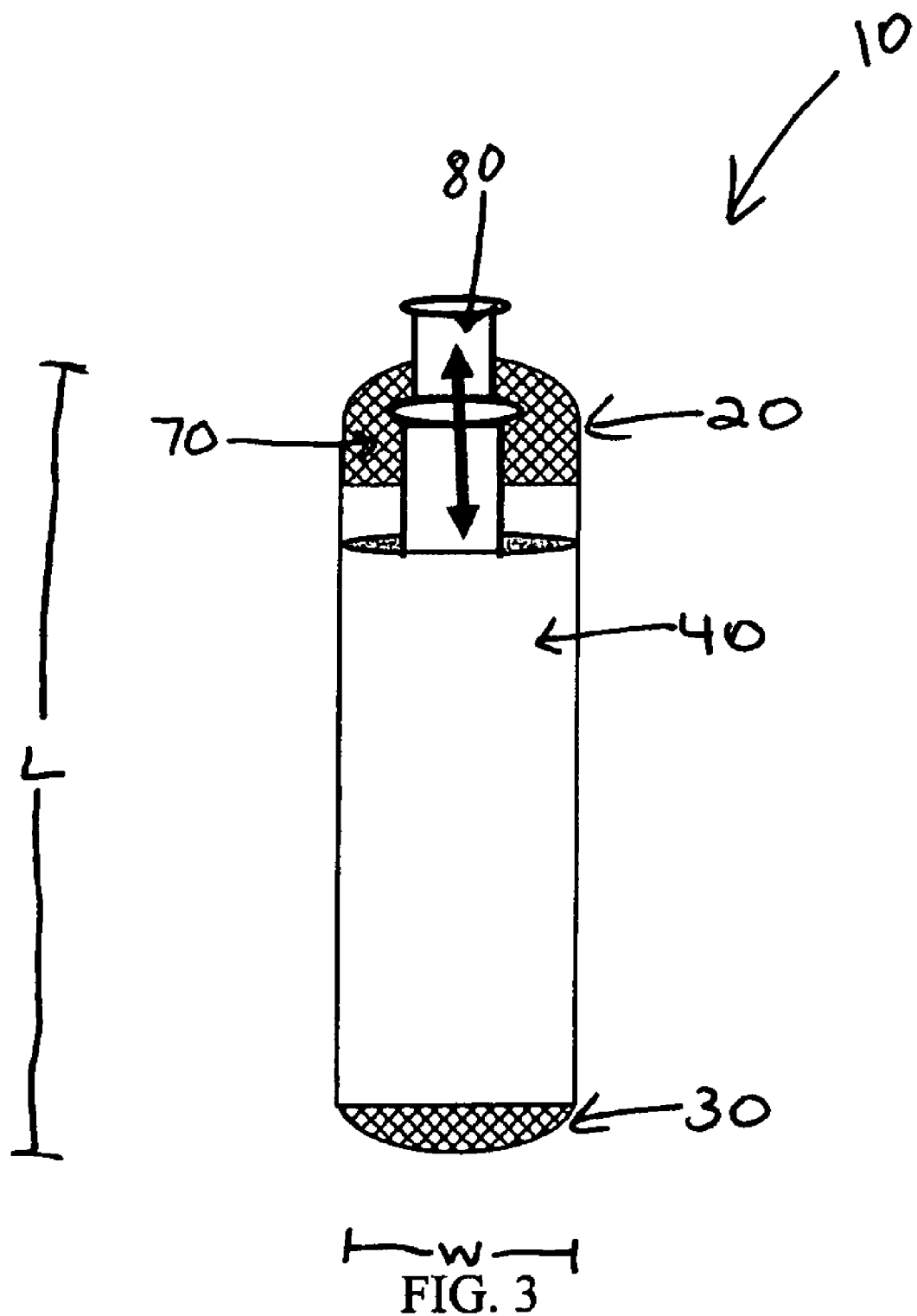
FIG. 3 is a plan view of one embodiment of the present invention.

FIG. 3 shows one embodiment of a wrapper 10, such as, for example, the wrapper 10 shown in FIG. 1. The wrapper 10 has a length L, a width W, a top 20, a bottom 30, and an outer surface 40 having a periphery. In this embodiment, the top seal 70 can be bent backward to break the line of weakness 50 to open the wrapper 10. Once the wrapper 10 is opened, the article 80 can be pushed up from the bottom 30 of the wrapper 10 and can be removed. As shown in FIG. 3, in this embodiment the wrapper 10 can remain in one piece after opening. After use, all or a portion of the article 80, such as, e.g., the applicator portion of a tampon, can be placed in the wrapper 10. In this embodiment, the top seal 70 can be used as a backstop as the article 80 is placed in the wrapper 10. In certain embodiments, the top seal 70 can be pulled forward over the used article 80 for increased discretion and cleanliness during transportation and/or disposal of the article 80.

Figure 4:
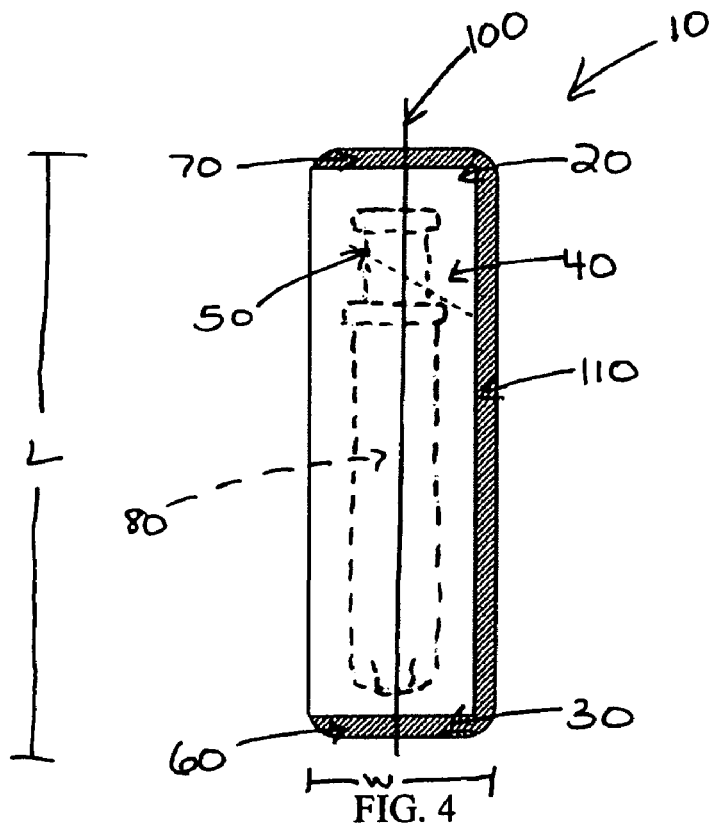
FIG. 4 is a plan view of one embodiment of the present invention.

FIG. 4 shows an embodiment of wrapper 10. The wrapper 10 has a length L, a width W, a top 20, a bottom 30, and an outer surface 40 having a periphery. In this embodiment, the wrapper 10 has a line of weakness 50 located in the upper third of the wrapper 10. The line of weakness 50 can be disposed on the wrapper 10 at an angle with respect to a longitudinal axis 100, such as, e.g., from the bottom 30 toward the top 20 of the wrapper 10. The line of weakness 50 can extend around less than about 95% of the periphery of the wrapper 10, such as, e.g., less than about 90%, less than about 85%, less than about 80%, less than about 75%, less than about 70%, less than about 65%, less than about 60%, less than about 55%, less than about 50%, less than about 45%, less than about 40%, or any other suitable amount of the periphery. The wrapper 10 can also have an end seal 60 located at the bottom 30 of the wrapper 10, a top seal 70 located at the top 20 of the wrapper 10, and or one or more side seals 110. An article for feminine hygiene 80, such as, e.g., a tampon, can be disposed within the wrapper 10.

Figure 5:
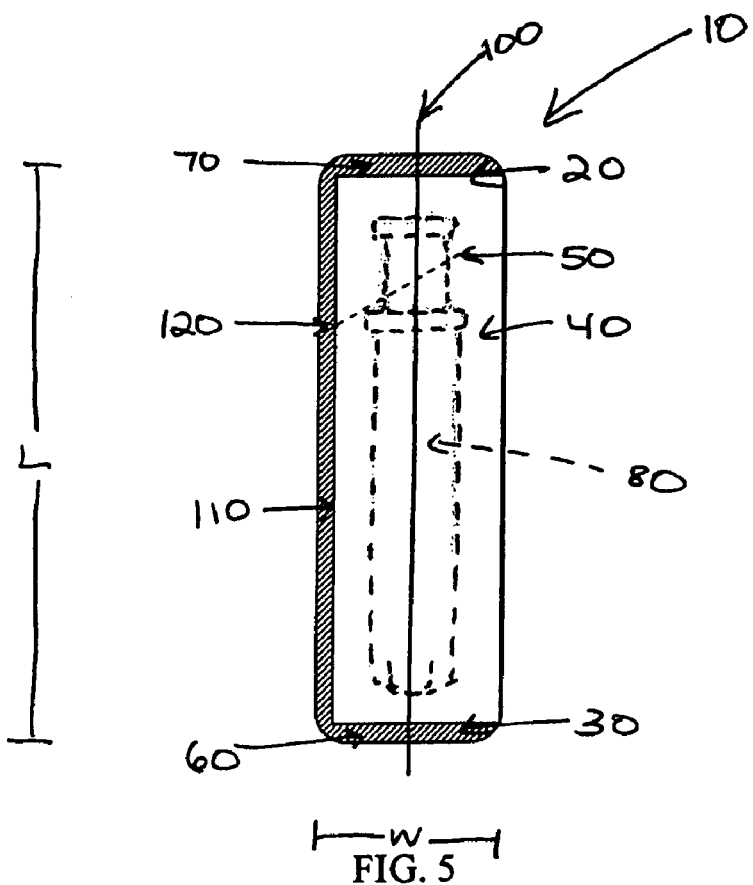
FIG. 5 is a plan view of one embodiment of the present invention.

FIG. 5 shows an embodiment of wrapper 10. The wrapper 10 has a length L, a width W, a top 20, a bottom 30, and an outer surface 40 having a periphery. In this embodiment, the wrapper 10 has a line of weakness 50 located in the upper third of the wrapper 10. The line of weakness 50 can be disposed on the wrapper 10 at an angle with respect to a longitudinal axis 100, such as, e.g., from the bottom 30 toward the top 20 of the wrapper 10. The line of weakness 50 can extend around less than about 95% of the periphery of the wrapper 10, such as, e.g., less than about 90%, less than about 85%, less than about 80%, less than about 75%, less than about 70%, less than about 65%, less than about 60%, less than about 55%, less than about 50%, less than about 45%, less than about 40%, or any other suitable amount of the periphery. The line of weakness 50 can have an initiation point 120, such as, e.g., a notch, slit, perforation, or other weakness point, that can reduce the force required for tear initiation at the initiation point 120 in order to break the line of weakness 50 and open the wrapper 10. The wrapper 10 can also have an end seal 60 located at the bottom 30 of the wrapper 10, a top seal 70 located at the top 20 of the wrapper 10, and or one or more side seals 110 on one or more sides. An article for feminine hygiene 80, such as, e.g., a tampon, can be disposed within the wrapper 10.

Figure 6:
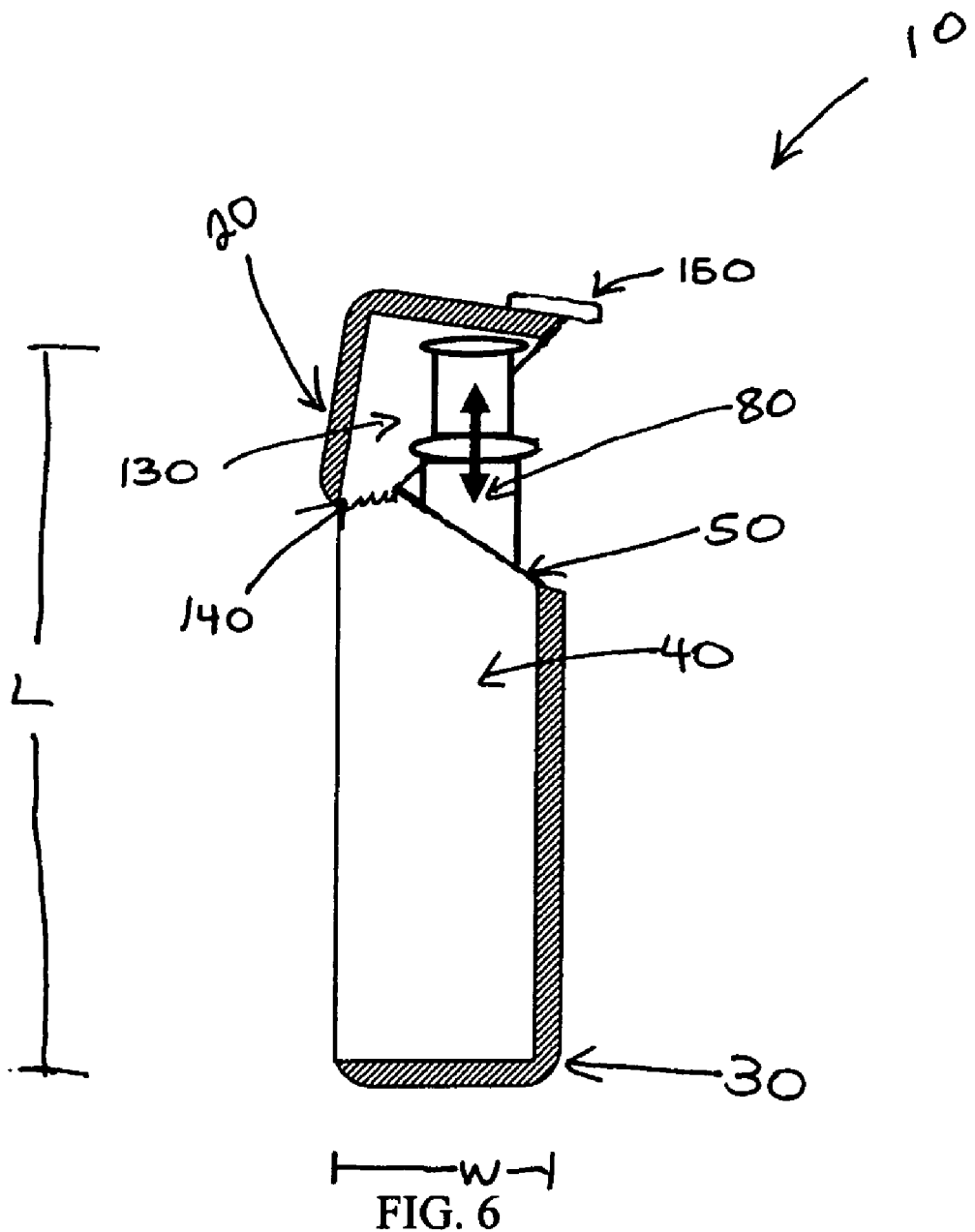
FIG. 6 is a plan view of one embodiment of the present invention.

FIG. 6 shows one embodiment of a wrapper 10. The wrapper 10 has a length L, a width W, a top 20, a bottom 30, and an outer surface 40 having a periphery. The top 20 of the wrapper 10 can be pulled to break the line of weakness 50 to open the wrapper 10, forming a hood 130 with a hinge 140 that can be formed from the unbroken portion of the wrapper 10. Once the wrapper 10 is opened, the article 80 can be grasped and removed. As shown in FIG. 6, in this embodiment the wrapper 10 can remain in one piece after opening. After use, all or a portion of the article 80, such as, e.g., the applicator portion of a tampon, can be placed in the wrapper 10. In this embodiment, the hood 130 can be disposed over the used article 80 or portion thereof for increased discretion and cleanliness during transportation and/or disposal. The wrapper 10 can also include means for sealing a portion of the wrapper 10 over the used article 80, such as, e.g., a tape tab 150 having a pressure sensitive adhesive disposed on one or more surfaces.

The wrapper 10 can have one or more lines of weakness. The one or more lines of weakness 50 can be located at any suitable location on the wrapper 10. In certain embodiments, the one or more lines of weakness 50 can be located near the top 20 of the wrapper 10, such as, e.g., at a location suitable to provide reduced exposure of the article 80 contained therein prior to use. As used herein, the "top of the wrapper" means the portion of the wrapper 10 nearest and/or covering the end of the article 80 that should be removed first from the wrapper 10. For example, when the article 80 is a tampon with an applicator, the top 20 of the wrapper 10 can be the portion of the wrapper 10 nearest and/or covering the portion of the applicator opposite the insertion end. In certain embodiments, the one or more lines of weakness 50 can be located in, for example, the upper half of the wrapper 10, the upper third of the wrapper 10, the upper fourth of the wrapper 10, the upper fifth of the wrapper 10, the upper sixth of the wrapper 10, or any other suitable location.

In certain embodiments, the one or more lines of weakness 50 can be located near the top 20 of the wrapper 10, such that the article 80 disposed within the wrapper 10 is not entirely exposed, such as, e.g., not entirely visible and/or not located above the opening, upon breaking the one or more lines of weakness 50 and/or opening the wrapper 10. For example, the one or more lines of weakness 50 can be located near the top 20 of the wrapper 10 such that less than about 50%, less than about 45%, less than about 40%, less than about 30%, less than about 25%, less than about 20%, less than about 15%, less than about 10%, less than about 5%, or less of the article 80 is exposed, such as, e.g., located above the opening, when the wrapper 10 is fully opened. In certain embodiments, the one or more lines of weakness 50 can be located near the top 20 of the wrapper 10 such that none of the article 80 is exposed, such as, e.g., located above the opening, when the wrapper 10 is fully opened.

The one or more lines of weakness 50 can encompass any amount of the width W and/or periphery of the wrapper 10 suitable to allow the wrapper 10 to remain in one piece after the wrapper 10 is fully opened. In certain embodiments, the one or more lines of weakness 50 can extend across less than the entire periphery of the wrapper 10, such as, e.g., less than about 95%, less than about 90%, less than about 85%, less than about 80%, less than about 75%, less than about 70%, less than about 65%, less than about 60%, less than about 55%, less than about 50%, less than about 45%, less than about 40%, or any other suitable amount of the periphery. The one or more lines of weakness 50 can be long enough to create an opening that is sufficiently large to allow the article 80 to be removed from the wrapper 10 upon opening of the wrapper 10.

The one or more lines of weakness 50 can be provided in any suitable pattern and/or direction. In certain embodiments, the one or more lines of weakness 50 can be provided across the wrapper 10, such as, e.g., transverse with respect to the length L of the wrapper 10. In addition or alternatively, the one or more lines of weakness 50 can be provided at an angle with respect to a longitudinal axis 100 of the wrapper 10. Any suitable angle can be used, such as, e.g., an angle upward from the initiation point 120 of the line of weakness 50 toward the top 20 of the wrapper 10 and/or an angle downward from the initiation point 120 of the line of weakness 50 toward the bottom 30 of the wrapper 10. Suitable angles include, e.g., from about 5° to about 85°, such as, e.g., from about 15° to about 75°, such as, e.g., from about 25° to about 65°, such as, e.g., from about 35° to about 55°.

A line of weakness 50 can be formed in any suitable manner, such as, e.g., mechanically and/or thermally, such as, for example, by using a laser and/or chemically. A line of weakness 50 can include a plurality of weakness points arranged in a row. The row can be straight, bent, angled, curved, and/or can change direction. In certain embodiments, one or more of the individual weakness points can overlap to form the line of weakness 50. In addition, or alternatively, one or more of the individual weakness points can be spaced apart from one another to form the line of weakness 50. In certain embodiments, an individual weakness point can be weaker than the surrounding area, such as, e.g., about 50% weaker, about 75% weaker, or about 100% weaker. The one or more lines of weakness 50 can be formed by perforations or by depressions. In certain embodiments, the one or more lines of weakness 50 can be sufficient to provide an opening for accessing the article 80, without the need for additional opening means, such as, e.g., a tear tape, stopper, and/or string.

The wrapper 10 can be comprised of any material suitable for wrapping articles for feminine hygiene 80. Suitable wrapper materials include, for example, flexible materials, such as, e.g., flexible polymeric films, such as, e.g., polymeric films made of polyethylene, polypropylene, polyester, cellophane, polyamide, polyvinyl chloride, ethylene-vinyl acetate copolymer, and/or other suitable films. In certain embodiments, the wrapper material can be heat-shrinkable films, stretch films or pre-stretched elastic material, such as, e.g., wrapper material that comprises polyolefins such as polyethylene and polypropylene, or polyvinyl chloride. Other suitable materials include, e.g., polystyrene, polyethylene-terephtalate (PET), and metallic foils, such as aluminium foil. Suitable materials can also include, e.g., non-occlusive or porous materials such as nonwovens, wovens, scrims, meshes and papers. Such non-occlusive materials can be made occlusive such as by lamination with or by coating with occlusive material. In the case of cellulosic papers, examples include lamination with a polymeric film such as a polyolefinic composition or coating or impregnation of the paper with wax. In certain embodiments, wrapper materials can be coated with various chemical compounds to improve their barrier properties or the ability for sealing. In addition, or alternatively, the wrapper material can have a low flexural modulus for providing a low noise wrapper 10 during transport as well as during handling and opening of the wrapper 10.

The wrapper 10 can be constructed in any suitable manner, such as, e.g., constructed of one connected piece of wrapper material or constructed from multiple pieces of material sufficiently joined together such that it substantially acts as one connected piece of wrapper material. In certain embodiments, the wrapper 10 can be formed by closing the wrapper material via heat-sealing onto itself after wrapping the article 80. In addition, or alternatively, the wrapper 10 can be glued, embossed, crimped, sewed, stitched, entangled, mechanically interlocked, cold pressure welded, ultrasonic bonded, and/or otherwise bonded or sealed.

The wrapper 10 can be any suitable color. In certain embodiments, the wrapper 10 can include one or more colors that correspond to a feature of the article 80, such as, e.g., absorbency, size, scent, lotion, or other features. For example, the article 80 can be a tampon and the wrapper 10 can include one or more colors that correspond to the absorbency of the tampon. In certain embodiments, the wrapper 10 can include one or more indica to provide a visual indication of the location of the one or more lines of weakness 50 on the wrapper 10. The indica can be any indicia suitable for providing a visual indication, such as, e.g., color, opacity, embossment, texture, or other suitable indicia. In certain embodiments, the indicia can be one or more colors suitable for indicating the location of the one or more lines of weakness 50, such as, e.g., one or more colors darker than, lighter than, and/or contrasting to one or more of the colors of the wrapper 10. The indicia can be one or more than one color. In certain embodiments, the indicia can be arranged in a pattern, such as, e.g., in a row. The indicia can be at any location suitable for indicating the location of the one or more lines of weakness 50, such as, e.g., at a location corresponding to the location of the one or more lines of weakness 50 and/or at a location near the one or more lines of weakness 50.

In certain embodiments, the wrapper 10 can include an opening aid, such as, e.g., means for making it easier for the user to open the wrapper 10. The opening aid can assist a user in removing an article 80 from the wrapper 10, e.g., by providing a means for the user to grip the wrapper 10 to break the one or more lines of weakness 50. The opening aid can be any suitable means, such as, e.g., one or more tabs, flaps, rings, caps, plates, curved plates, sticks, discs, asymmetrical structures, meshes, screens, flared structures, molded parts, cut or stamped sheet, or any other suitable opening aid, such as, e.g., opening aids described in U.S. Pat. No. 6,955,665 (Domeler, et al.). The opening aid can be at any suitable location on the wrapper 10, such as, e.g., the top 20 of the wrapper 10, one or more sides of the wrapper 10, and/or the bottom 30 of the wrapper 10.

The opening aid can include one or more tabs. The one or more tabs can be formed from a portion of the wrapper 10. Alternatively, or in addition, the one or more tabs can extend from the outer surface 40 of the wrapper material, such as, e.g., as a portion of wrapper material protruding from the wrapper 10. A tab can be any suitable size. In certain embodiments, a tab will be sufficiently large to be reliably grasped by the user, such as, e.g., as a tab, handle or finger grip. In certain embodiments, a tab can be stiffened, e.g., by heat sealing, and/or embossing with or without the addition of heat. In certain embodiments, the tab can also function as a seal. For example, in certain embodiments, the wrapper 10 can include one or more lines of weakness 50 that can be transverse with respect to the length L of the applicator and a top seal 70 that can function as a tab and/or a finger grip. In this example, the user can grip the tab and pull or bend the tab to break the one or more lines of weakness 50. In certain embodiments, a portion of the article 80, such as, e.g., an end of a tampon article 80, can act to provide an opposing force to facilitate breaking of the one or more lines of weakness 50 when the tab is bent or pulled.

A method of removing an article 80 from a wrapper 10 is also provided. In certain embodiments, the method includes gripping the wrapper 10, breaking the one or more lines of weakness 50 to form an opening configured to release the article 80. The user can then grasp the article 80 and remove it from the wrapper 10, or alternatively, or in addition, push the article 80 up from the bottom 30 of the wrapper 10 such that at least a portion of the article 80 can be grasped by the user. The wrapper 10 can remain in one piece after the one or more lines of weakness 50 are broken to form an opening.

In certain embodiments, a user will have at least a portion of an article 80 for disposal after use. The user can place the at least a portion of the used article 80 into the wrapper 10 for disposal. For example, where the wrapper 10 includes an opening aid, the opening aid can in certain embodiments, act to facilitate placement of the used article 80 or portion thereof into the wrapper 10, such as, e.g., by acting as a backstop. In certain embodiments, a portion of the wrapper 10, such as, e.g., the top 20 of the wrapper 10, can be pulled over the at least a portion of the used article 80 once it is placed into the wrapper 10 for transportation and/or disposal, such as, e.g., to provide increased discretion and cleanliness during transportation and/or disposal.

In certain embodiments, the wrapper 10 can include a means for sealing a portion of the wrapper 10 over the at least a portion of the used article 80 once it is placed into the wrapper 10 for transportation and/or disposal. Any suitable means for sealing the wrapper 10 can be used, such as, e.g., adhesive, glues, tapes, thermal bonds, and/or mechanical fasteners. In certain embodiments, the means can include a portion of the surface of the wrapper 10 could be covered with adhesive, cohesive, or other joining means. In addition, or alternatively, the means can include a sealing tab 150 having a pressure sensitive adhesive or other suitable closure means disposed on one or more surfaces.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A package, comprising:
    a reusable wrapper comprising wrapper material, a length, a top, a bottom, a top seal at the top, an end seal at the bottom, a third seal extending along the length, an outer surface having a circumferential periphery that is oriented substantially orthogonal to the length, a longitudinal axis, and one or more predetermined lines of weakness extending along the circumferential periphery around the reusable wrapper but to an extent that is less than about 95% of the circumferential periphery of the outer surface of the wrapper; and
    an article for feminine hygiene enclosed in the wrapper,
    wherein a portion of the one or more predetermined lines of weakness intersect with the third seal,
    wherein the article comprises an applicator tampon,
    wherein the article can be released by breaking the one or more lines of weakness to form an opening,
    wherein less than about 50% of the article is located above the opening when the article is disposed in the wrapper at a position most proximal to the bottom of the wrapper;

wherein the wrapper remains in one piece after the one or more lines of weakness are broken; and wherein the reusable wrapper is adapted to receive through the opening at least a portion of the article after use of the article through the opening to re-enclose the portion of the article in the wrapper.

2. The package of claim 1, wherein the reusable wrapper further comprises a sealing portion for resealing the reusable wrapper after receiving at least a portion of the article after use of the article.

3. The package of claim 1, wherein the applicator tampon is a compact applicator tampon.

4. The package of claim 1, wherein the reusable wrapper further comprises indicia proximate the one or more lines of weakness to provide a visual indication of the location of the one or more lines of weakness, the indicia comprising a color that is darker and/or contrasts with a color of the wrapper material.

5. The package of claim 1, wherein the wrapper material comprises a polymeric film.

6. The package of claim 1, wherein at least one of the top seal, the end seal, and the third seal comprises a crimp or embossed seal.

7. The package of claim 1, wherein each of the top seal, the end seal, and the third seal comprises a crimp or embossed seal.

8. A package, comprising:
a reusable wrapper comprising a length, a top, a bottom, a top seal proximate the top, an end seal proximate the bottom, an outer surface having a circumferential periphery that is oriented substantially orthogonal to the length, and one or more predetermined lines of weakness extending around the circumferential periphery but less than the entire circumferential periphery the circumferential periphery of the outer surface of the wrapper; and
a tampon applicator enclosed in the wrapper, the tampon applicator including a body insertion member and a plunger slidably disposed within the body insertion member,
wherein the tampon applicator can be released by breaking the one or more lines of weakness to form an opening,
wherein at least a portion of the plunger is located above the opening and the body insertion member is located below the opening when the tampon applicator is disposed in the wrapper at a position most proximal to the bottom of the wrapper;
wherein the wrapper is capable of remaining in one piece after the one or more lines of weakness are broken; and
wherein the reusable wrapper is adapted to receive a used tampon applicator through the opening after the tampon applicator has been removed.

9. The package of claim 8, wherein the one or more predetermined lines of weakness extend around less than about 95% of the circumferential periphery.

10. The package of claim 8, wherein the one or more predetermined lines of weakness extend around less than about 90% of the circumferential periphery.

11. The package of claim 8, wherein the one or more predetermined lines of weakness extend around less than about 85% of the circumferential periphery.

12. The package of claim 8, wherein the one or more predetermined lines of weakness extend around less than about 80% of the circumferential periphery.

13. The package of claim 8, wherein the tampon applicator tampon is a compact applicator.

14. The package of claim 8, wherein the reusable wrapper further comprises indicia proximate the one or more lines of weakness to provide a visual indication of the location of the one or more lines of weakness, the indicia comprising a color that is darker and/or contrasts with a color of a material from which the reusable wrapper is made.

15. The package of claim 8, wherein the reusable wrapper comprises a polymeric film.

16. The package of claim 8, wherein the reusable wrapper further comprises a third seal extending along the length, and wherein the one or more lines of weakness intersect the third seal.

17. A package, comprising:
a wrapper comprising a length, a top, a bottom, a circumferential periphery that is oriented substantially orthogonal to the length, a line of weakness extending around the circumferential periphery but less than the entire circumferential periphery the circumferential periphery, a top seal proximate the top, an end seal proximate the bottom, and a third seal extending along the length, wherein the one or more lines of weakness intersect the third seal; and
a tampon applicator enclosed in the wrapper, the tampon applicator including a body insertion member and a plunger slidably disposed within the body insertion member,
wherein the plunger is positioned proximate to the line of weakness and the body insertion member is positioned distal to the line of weakness,
wherein the tampon applicator can be released by breaking the one or more lines of weakness to form an opening, and
wherein at least a portion of the plunger is located above the opening and the body insertion member is located below the opening when the tampon applicator is disposed in the wrapper at a position most proximal to the bottom of the wrapper.

18. The package of claim 17, wherein the line of weakness extends around less than about 95% of the circumferential periphery.

19. The package of claim 17, wherein the line of weakness extends around less than about 90% of the circumferential periphery.

20. The package of claim 17, wherein the line of weakness extends around less than about 80% of the circumferential periphery.

21. The package of claim 17, wherein the wrapper further comprises indicia proximate the line of weakness to provide a visual indication of the location of the line of weakness, the indicia comprising a color that is darker and/or contrasts with a color of a material from which the wrapper is made.

* * * * *

UNITED STATES PATENT AND TRADEMARK OFFICE
CERTIFICATE OF CORRECTION

| | | |
|---|---|---|
| PATENT NO. | : 8,302,844 B2 | Page 1 of 1 |
| APPLICATION NO. | : 11/602112 | |
| DATED | : November 6, 2012 | |
| INVENTOR(S) | : Kimberly Nichole McConnell et al. | |

It is certified that error appears in the above-identified patent and that said Letters Patent is hereby corrected as shown below:

Column 9

Lines 35-36, delete "the circumferential periphery". It is duplicative.

Column 10

Line 25, delete "the circumferential periphery". It is duplicative.

Signed and Sealed this
Nineteenth Day of March, 2013

Teresa Stanek Rea
*Acting Director of the United States Patent and Trademark Office*